(12) United States Patent
Liu

(10) Patent No.: US 9,370,633 B2
(45) Date of Patent: Jun. 21, 2016

(54) NASAL INTERMITTENT MANDATORY VENTILATION (NIMV) CONTROL SYSTEM IN A VENTILATOR

(75) Inventor: Yong Liu, Yorba Linda, CA (US)

(73) Assignee: CareFusion 207, Inc., San Diego, CA (US)

( * ) Notice: Subject to any disclaimer, the term of this patent is extended or adjusted under 35 U.S.C. 154(b) by 510 days.

(21) Appl. No.: 12/880,022

(22) Filed: Sep. 10, 2010

(65) Prior Publication Data

US 2012/0060837 A1 Mar. 15, 2012

(51) Int. Cl.
*A61M 16/00* (2006.01)
*A61M 16/06* (2006.01)

(52) U.S. Cl.
CPC ....... *A61M 16/0051* (2013.01); *A61M 16/0672* (2014.02); *A61M 2016/0039* (2013.01); *A61M 2016/0042* (2013.01); *A61M 2205/52* (2013.01)

(58) Field of Classification Search
CPC .......... A61M 16/20; A61M 2016/204; A61M 16/0015; A61M 16/0018; A61M 16/0027; A61M 16/003; A61M 16/0057; A61M 16/0069
USPC .............. 128/204.18, 204.21, 204.23, 204.26
See application file for complete search history.

(56) References Cited

U.S. PATENT DOCUMENTS

| 4,838,257 | A | 6/1989 | Hatch | |
|---|---|---|---|---|
| 5,797,393 | A * | 8/1998 | Kohl | 128/204.23 |
| 5,931,162 | A | 8/1999 | Christian | |
| 6,105,575 | A * | 8/2000 | Estes et al. | 128/204.23 |
| 6,439,229 | B1 | 8/2002 | Du et al. | |
| 6,564,798 | B1 | 5/2003 | Jalde | |
| 8,161,972 | B2 * | 4/2012 | Isaza | 128/207.16 |
| 8,474,455 | B2 * | 7/2013 | Soliman | A61M 16/0051 128/200.24 |
| 2002/0020410 | A1 * | 2/2002 | Rydin et al. | 128/200.24 |
| 2007/0144516 | A1 * | 6/2007 | Doyle | 128/204.18 |
| 2009/0293876 | A1 * | 12/2009 | Soliman | A61M 16/0096 128/204.22 |
| 2011/0126832 | A1 * | 6/2011 | Winter et al. | 128/204.21 |

OTHER PUBLICATIONS

International Search Report and Written Opinion for PCT/US2011/047301 mailed Mar. 19, 2012.

* cited by examiner

*Primary Examiner* — Justine Yu
*Assistant Examiner* — LaToya M Louis
(74) *Attorney, Agent, or Firm* — McDermott Will & Emery LLP

(57) ABSTRACT

A ventilator including an inspiration flow control unit and an expiration flow control unit coupled to the inspiration flow control unit. The ventilator also includes a nasal intermittent mandatory ventilation (NIMV) control system coupled to the inspiration flow control unit and the expiration flow control unit. The NIMV control system is configured to automatically and simultaneously adjust an inspiration flow and an expiration flow. A pressure of the inspiration flow is increased from a baseline pressure to a control pressure. A pressure of the expiration flow is returned to the baseline pressure.

7 Claims, 4 Drawing Sheets

NASAL INTERMITTENT MANDATORY VENTILATION (NIMV) CONTROL SYSTEM IN A VENTILATOR

BACKGROUND

Ventilators often incorporate continuous positive airway pressure (CPAP) to facilitate breathing for a patient. However, CPAP can have many drawbacks. For example, medical practitioners often are required to manually adjust the ventilator and it may be difficult for a neonate to breath against the CPAP.

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Figure 1:
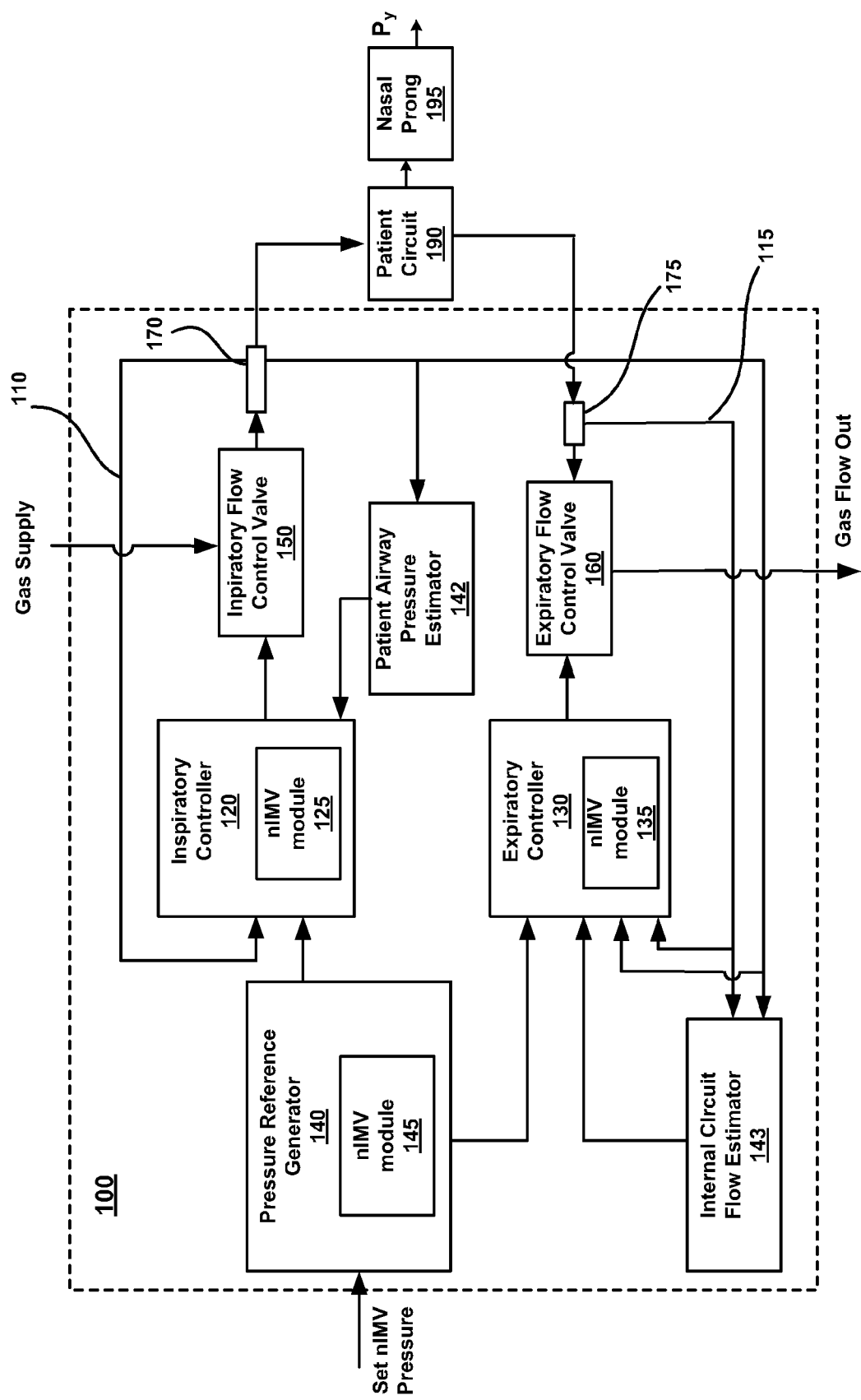
FIG. 1 illustrates an example of a ventilator, in accordance with an embodiment of the present invention.

FIG. 1 depicts a ventilator 100, in accordance to an embodiment of the present invention. A discussion regarding embodiments of ventilator 100 is provided below. First, the discussion will describe the structure or components of various embodiments of ventilator 100. Then the discussion will describe the operational description of ventilator 100

Ventilator 100 includes inspiratory controller 120, expiratory controller 130, pressure reference generator 140, inspiratory flow control valve (IFCV) 150, and expiratory flow control valve (EFCV) 160. The combination of inspiratory controller 120 and IFC 150 can be referred to as an inspiratory control unit. Similarly, the combination of expiratory controller 130 and EFCV 160 can be referred to as an expiratory control unit.

Ventilator 100 also includes a nasal intermittent mandatory ventilation (NIMV) control system. The NIMV control system comprises the combination of NIMV modules 125-145 associated with inspiratory controller 125, expiratory controller 135 and pressure reference generator, respectively. The NIMV control system is configured to automatically and simultaneously adjust an inspiration flow and an expiration flow.

During use, a patient (not shown) is coupled to ventilator 100 via patient circuit 190 and nasal prong 195. In one embodiment, patient circuit 190 is a dual limb circuit. For example, patient circuit 195 includes an inspiratory limb (not shown) associated with the inspiratory flow control unit and an expiratory limb (not shown) associated with the expiratory flow control unit.

In general, the NIMV control system facilitates in generating time-triggered, time-cycled mandatory breathes through nasal prong 195 or cannula with positive pressure applied to entire respiratory cycles. Each breath comprises an inspiratory phase and expiratory phased. During the inspiratory phase the control pressure is increased from a baseline pressure to a control pressure. The control pressure is a baseline pressure plus an inspiratory pressure. During the expiratory phase the control pressure is returned to the baseline pressure.

The NIMV pressure through IFCV 150 and EFCV 160 is controlled simultaneously by IFCV 150 and EFCV 160. Both IFCV 150 and EFCV 160 are coupled and in fluid communication with the patient airway.

Air flow into and out of patient circuit 190 is measured by inspiration flow sensor 170 and expiration flow sensor 175, respectively. For example, inspiration flow 110 is measured by inspiration flow sensor 170 and expiration flow 115 is measured by expiration flow sensor 175. Moreover, sensors 170 and 175 can also measure the inspiration pressure and expiration pressure, respectively. The sensed flow and pressure signals provide feedback information to both IFCV 150 and EFCV 160.

Accordingly, inspiratory controller 120 and expiratory controller 130 automatically regulate the amount of air flowing through patient circuit 190, such that ventilator 100 maintains a baseline pressure (e.g., CPAP pressure) or inspiration pressure. In one embodiment, the baseline pressure and inspiration pressure are delivered following NIMV settings, such as, breath rate, inspiration time, rising time setting, etc.

In one embodiment, patient airway pressure 192 is estimated by patient airway pressure estimator 142. For instance, the estimation is facilitated by internal sensor measurement and patient circuit characterization. Thus, the pressure delivery accuracy is guaranteed and a patient airway pressure sensor is not required.

Internal circuit flow estimator 143 estimates the airflow of a spontaneous breath of the patient, while the airway pressure of the patient is continuously changing. In other words, internal circuit flow estimator 143 utilizes, among other things, the inspiration pressure measurement, inspiration flow measurement 110, expiration flow 115 and circuit characterization (which is the pressure drop for the circuit under certain flow) to estimate the patient pressure.

Accordingly, the NIMV control system is able to automatically adjust the amount of airflow through patient circuit 190, such that ventilator 100 is able to deliver controlled airway pressure without manually adjustment in order to satisfy a patients needs.

In one embodiment, pressure reference generator 140 generates a pressure reference signal, $P_r$. $P_r$ is the command signal for both IFCV 150 and EFCV 160. $P_r$ is generated based on, but not limited to, $P_{CPAP}$ (set CPAP level), $P_{insp}$ (set inspiration level), inspiration time and rising time setting.

Figure 2:
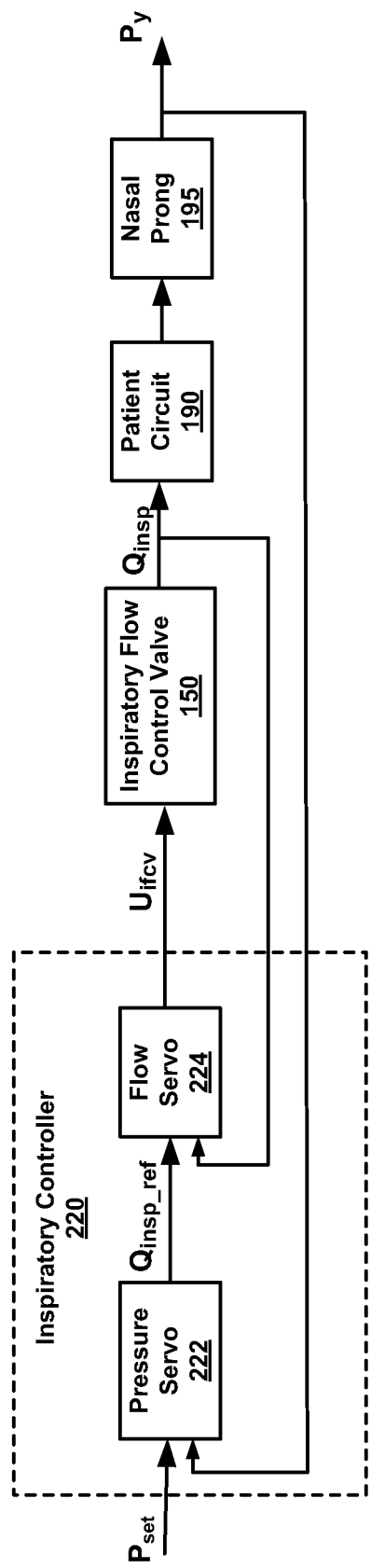
FIG. 2 illustrates an example of an inspiratory controller, in accordance with an embodiment of the present invention.

FIG. 2 depicts inspiratory controller 220, in accordance to an embodiment of the present invention. Inspiratory controller 220 includes pressure servo 222 and flow servo 224.

Pressure servo 222 generates flow reference, $Q_{insp\_ref}$. Flow servo 224 generates $U_{ifcv}$, which is the command to IFCV 150. $Q_{insp}$ is the flow measured by inspiratory flow sensor 170.

During a patient's inspiration, pressure servo 222 increases $Q_{insp\_ref}$ such that flow servo 224 provides more gas for patient circuit 190. During expiration, $Q_{insp\_ref}$ decreases, resulting in flow servo 224 reducing circuit flow such that the patient may exhale easier. Accordingly, inspiratory controller 220 prevents large fluctuations of airway pressure due to a patient's efforts.

Figure 3:
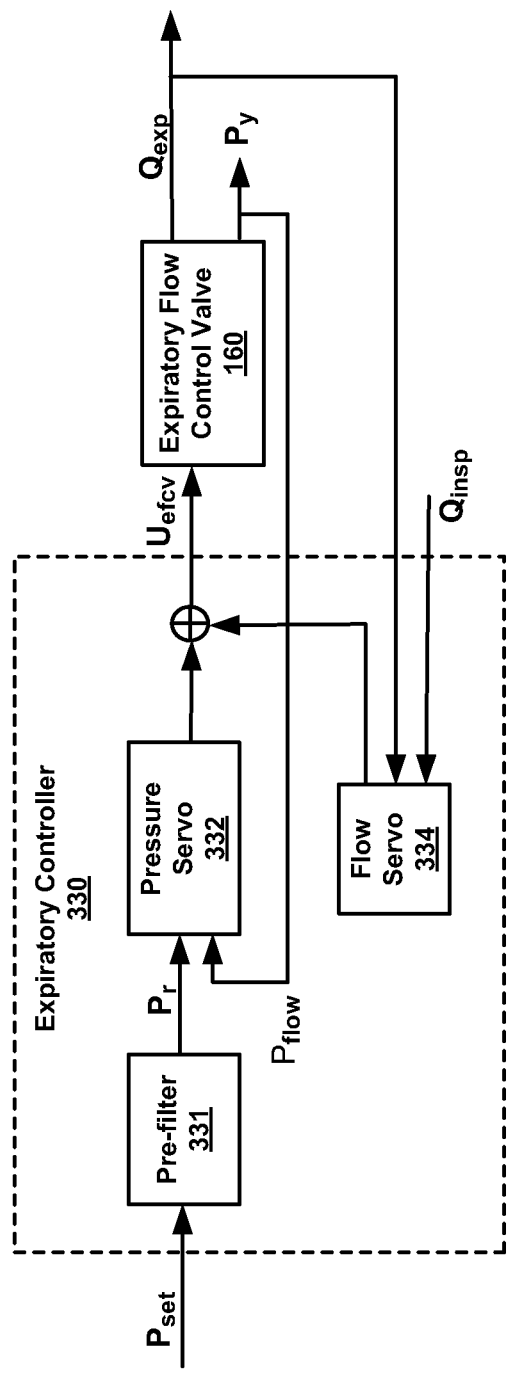
FIG. 3 illustrates an example of an expiratory, in accordance with an embodiment of the present invention.

FIG. 3 depicts an embodiment of expiratory controller 330, in accordance to an embodiment of the present invention. Expiratory controller 330 includes pre-filter 331, pressure servo 332 and flow servo 334. Expiratory controller 330 generates $U_{efcv}$, which is the command to EFCV 160.

In one embodiment, pressure servo 332 is a proportional integral (PI) control plus a feedforward term. Flow servo 334 is configured to generate an additional command to pressure servo 332. As shown in FIG. 3, the output of flow servo 334 is added to the output of pressure servo 332. The sum is sent to EFCV 160. The output of flow servo 334 is an additional term to the pure pressure servo 332.

The NIMV circuit flow is restrained to a command flow rate by controlling exhalation flow. Further, the command flow rate is obtained from internal circuit flow estimator 143 by monitoring the minimum values of the inspiratory flow 110 and expiratory flow 115. A flow generator is able to automatically select a suitable NIMV circuit flow reference, $Q_{CPAP}$, according to a patient's need. Moreover, EFCV 160 is able to facilitate in regulating the circuit pressure and simultaneously facilitate in controlling the amount of air running through patient circuit 190.

In contrast, in conventional systems, the exhalation valve is a normally an open, force balanced poppet type valve. Due to the location of the exhalation valve at the downstream of the circuit, the valve's upstream pressure, i.e., the circuit pressure acting on the valve poppet is balanced by the applied force plus any flow forces on the poppet in the direction against the flow. Accordingly, the pressure equilibriums can be established under different flow rates.

Although a conventional exhalation pressure controller is able to generate a counterbalance force for maintaining a desired pressure level, the poppet of the valve may locate at arbitrary position. In other words, when such an exhalation pressure controller is used together with the inspiratory pressure servo, the circuit flow is uncontrollable. As a result, the poppet is often pushed to its maximum limit. Consequently, the circuit flow will also increase to its maximum limit.

Figure 4:
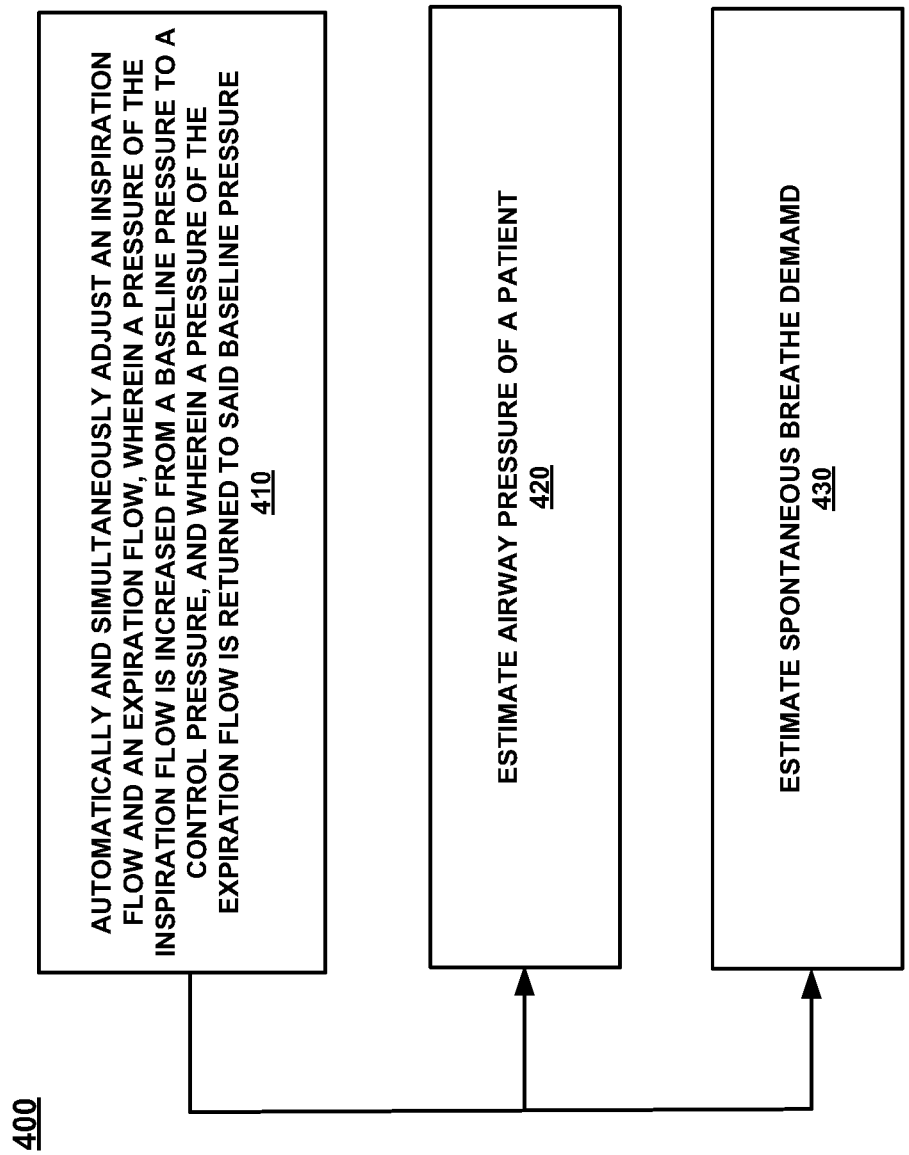
FIG. 4 illustrates an example of a flow chart of a method for NIMV in a ventilator, in accordance with an embodiment of the present invention.

FIG. 4 depicts method 400 for NIMV in a ventilator, in accordance with an embodiment of the present invention. In various embodiments, method 400 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 400 is performed at least by ventilator 100 as described in FIG. 1.

At 410 of method 400, an inspiration flow and an expiration flow automatically and simultaneously adjusted, wherein a pressure of the inspiration flow is increased from a baseline pressure to a control pressure, and wherein a pressure of the expiration flow is returned to the baseline pressure.

In one embodiment, at 420 of method 400, the airway pressure of a patient is estimated. For example, patient airway pressure estimator 142 estimates the airway pressure of the patient.

In another embodiment, at 430 of method 400, the spontaneous breathe demand is estimated. For example, internal flow estimator estimates the spontaneous breath demand.

Various embodiments of the present invention are thus described. While the present invention has been described in particular embodiments, it should be appreciated that the present invention should not be construed as limited by such embodiments, but rather construed according to the following claims.

The invention claimed is:

1. A nasal intermittent mandatory ventilation (NIMV) control system comprising:
a first NIMV module associated with an inspiration flow control unit; and
a second NIMV module associated with an expiration flow control unit,
wherein said inspiration flow control unit is coupled to said expiration flow control unit,
wherein said NIMV control system is configured to automatically and simultaneously adjust an inspiration flow through an inspiration flow control valve and an expiration flow through an expiration flow control valve,
wherein said expiration flow control unit comprises a pressure servo and a flow servo, the flow servo being configured to receive a measurement from an inspiration flow sensor and a separate measurement from an expiration flow sensor, and said expiration flow control unit is configured to add an output of the flow servo to an output of the pressure servo,
wherein the inspiration flow control unit comprises an additional pressure servo and an additional flow servo, the additional pressure servo and the additional flow servo being separate from the pressure servo and the flow servo of the expiration flow control unit,
wherein the additional pressure servo is configured to generate a flow reference and provide the flow reference to the additional flow servo,
wherein the additional flow servo is configured to generate a command for the inspiration flow control valve based on the flow reference and the measurement from the inspiration flow sensor such that the inspiration flow control unit comprises an internal feedback loop for the additional flow servo within an external feedback loop for the additional pressure servo,
wherein the output from the flow servo of the expiration flow control unit is based on the measurement from the inspiration flow sensor and the separate measurement from the expiration flow sensor,
wherein said expiration flow control valve is operatively coupled to said expiration flow control unit and is a separate valve assembly from said inspiration flow control valve,
wherein a pressure of said inspiration flow is increased from a baseline pressure to a control pressure, and
wherein a pressure of said expiration flow is returned to said baseline pressure.

2. The NIMV control system of claim 1, comprising:
a third NIMV module associated with a pressure reference generator.

3. A ventilator comprising:
an inspiration flow control unit;
an expiration flow control unit coupled to said inspiration flow control unit;

an internal circuit flow estimator; and a nasal intermittent mandatory ventilation (NIMV) control system coupled to said inspiration flow control unit and said expiration flow control unit, wherein said NIMV control system is configured to automatically and simultaneously adjust an inspiration flow through an inspiration flow control valve and an expiration flow through an expiration flow control valve, wherein said expiration flow control unit comprises a pressure servo and a flow servo, the flow servo being configured to receive a measurement from an inspiration flow sensor and a separate measurement from an expiration flow sensor, and said expiration flow control unit is configured to add an output of the flow servo to an output of the pressure servo, wherein the output from the flow servo is based on the measurement from the inspiration flow sensor and the separate measurement from the expiration flow sensor, wherein said expiration flow control valve is operatively coupled to said expiration flow control unit and is a separate valve assembly from said inspiration flow control valve, wherein a pressure of said inspiration flow is increased from a baseline pressure to a control pressure, wherein a pressure of said expiration flow is returned to said baseline pressure, and wherein said internal circuit flow estimator is configured to generate a command flow according to a patient's need by monitoring minimum values of the measurement from the inspiration flow sensor and the separate measurement from the expiration flow sensor, wherein the inspiration flow control unit comprises an additional pressure servo and an additional flow servo, the additional pressure servo and the additional flow servo being separate from the pressure servo and the flow servo of the expiration flow control unit, wherein the additional pressure servo is configured to generate a flow reference and provide the flow reference to the additional flow servo, and wherein the additional flow servo is configured to generate a command for the inspiration flow control valve based on the flow reference and the measurement from the inspiration flow sensor such that the inspiration flow control unit comprises an internal feedback loop for the additional flow servo within an external feedback loop for the additional pressure servo.

4. The ventilator of claim 3, comprising:

a patient airway pressure estimator configured to estimate airway pressure of a patient.

5. The ventilator of claim 4, wherein said NIMV control system is configured to automatically and simultaneously adjust said inspiration flow through said inspiration flow control valve and said expiration flow through said expiration flow control valve based, in part, on said estimated airway pressure.

6. The ventilator of claim 3, wherein said internal flow estimator is configured to estimate spontaneous breath demand flow.

7. The ventilator of claim 6, wherein said NIMV control system is configured to automatically and simultaneously adjust said inspiration flow through said inspiration flow control valve and said expiration flow through said expiration flow control valve based, in part, on said estimated spontaneous breathe demand flow.

* * * * *